United States Patent [19]

Fahey

[11] 4,124,627

[45] Nov. 7, 1978

[54] TRANS-FLUORO(PENTAFLUORO-PHENYL)-BIS(TRIETHYLPHOSPHINE)-NICKEL(II)

[75] Inventor: Darryl R. Fahey, Bartlesville, Okla.

[73] Assignee: Phillips Petroleum Company, Bartlesville, Okla.

[21] Appl. No.: 822,182

[22] Filed: Aug. 5, 1977

[51] Int. Cl.$^2$ ............................................. C07F 15/04
[52] U.S. Cl. ...................... 260/439 R; 260/683.15 D
[58] Field of Search ................................... 260/439 R

[56] References Cited

U.S. PATENT DOCUMENTS

| 3,686,245 | 8/1972 | Fahey | 260/439 R |
|---|---|---|---|
| 3,800,000 | 3/1974 | Fahey | 260/439 R |
| 3,808,246 | 4/1974 | Fahey | 260/439 R |
| 3,818,063 | 6/1974 | Fahey | 260/439 R |
| 3,887,441 | 6/1975 | Hughes et al. | 260/439 R |
| 3,903,120 | 9/1975 | Shook et al. | 260/439 R |
| 4,055,582 | 10/1977 | Fahey | 260/439 R |

*Primary Examiner*—Helen M. S. Sneed

[57] ABSTRACT

A composition comprising trans-fluoro(pentafluorophenyl)bis(triethylphosphine)nickel(II) and methods for preparing same are disclosed.

13 Claims, No Drawings

TRANS-FLUORO(PENTAFLUOROPHENYL)-BIS(-TRIETHYLPHOSPHINE)NICKEL(II)

This invention relates to a new composition of matter, transfluoro(pentafluorophenyl)bis(triethylphosphine)nickel(II). In another aspect this invention relates to methods of producing trans-fluoro(pentafluorophenyl)bis(triethylphosphine)nickel(II).

The oxidative-addition of organic chlorides, bromides, and iodides to low valent transition metal complexes is an important method of synthesis in organometallic chemistry. The reaction is often facile with organic iodides and usually very difficult with organic chlorides. No examples are known in the prior art of such an oxidative-addition involving a carbon-fluorine bond. For example, the oxidative-addition of pentafluorochlorobenzene or pentafluorobromobenzene to 1,5-cyclooctadienebis(triethylphosphine)-nickel(O) results in the formation of pentafluorophenylbis(triethylphosphine) nickel(II) chloride or bromide respectively. Further, as shown in *Journal of Organometallic Chemistry*, 84, 93–103 (1975), the oxidative-addition of bromobenzene and chlorobenzene to diethyl(dipyridyl)nickel(O) result in the corresponding aryl(dipyridyl)nickel(II) halide, while the oxidative-addition of fluorobenzene does not occur under similar reaction conditions.

An object of the present invention is to provide a fluoro(pentafluorophenyl)bis(triethylphosphine)nickel(II) complex.

Another object of the present invention is to provide methods for producing fluoro(pentafluorophenyl)bis(triethylphosphine)nickel(II) complex.

Further aspects, objects, and advantages of the present invention will be apparent from the disclosure and the appended claims.

In accordance with the present invention trans-fluoro(pentafluorophenyl)bis(triethylphosphine)nickel(II) is produced by reacting hexafluorobenzene and a nickel complex selected from the group consisting of tetrakis(triethylphosphine)nickel(O), ethylenebis(triethylphosphine)nickel(O), and (1,5-cyclooctadiene)bis(triethylphosphine)nickel(O).

The reaction is conducted in a suitable solvent. Any solvent can be employed which does not prevent the formation of the desired product. The amount of solvent needed is generally an amount which will insure that reactants are in solution during the reaction. One skilled in the art having the benefit of this disclosure can readily vary the concentration of reactants in various suitable solvents to obtain different reaction rates and thus different yields of the product. Examples of suitable solvents include aliphatic hydrocarbons, aromatic hydrocarbons, ethers, aliphatic nitriles, aliphatic ketones, alkyl esters of aliphatic acids, and mixtures of any two or more thereof. Typical specific examples of suitable solvents include hexane, heptane, octane, benzene, toluene, xylenes, dioxane, diethyl ether, tetrahydrofuran, diethylene glycol dimethyl ether, acetonitrile, propionitrile, butyronitrile, acetone, methyethyl ketone, diethyl ketone, methyl acetate, ethyl acetate, methyl propionate, and mixtures of any two or more thereof.

While some of the desired product may be produced at higher or lower temperatures generally the reaction is carried out at a temperature in the range of about 0° C. to about 125° C., preferably in the range of about 20° C. to about 75° C. Generally any pressure can be employed which allows the reactants to be reacted in solution. In general, the pressure will be in the range of about 5 to about 1000 psia, and atmospheric pressure is preferred. Reaction time is generally in the range of about 15 minutes to about 14 days, preferably in the range of about 30 minutes to about 8 days. It is to be noted that operation in the lower end of the temperature range can be expected to be associated with reaction periods in the upper end of the reaction time range and vice versa.

In the practice of the present invention generally the molar ratio of hexafluorobenzene to nickel complex reactant is in the range of about 5:1 to about 1:1, preferably about 2:1 to about 1:1.

The hexafluorobenzene and the nickel complex reactants can be prepared using any suitable techniques known in the art. A preferred embodiment of the present invention involves utilizing the product mixture which results when bis(1,5-cyclooctadiene)nickel(O) and triethylphosphine are contacted in a suitable solvent to yield a product mixture containing 1,5-cyclooctadienebis(triethylphosphine)nickel(O). Generally in preparing such a product mixture the molar ratio of the bis(1,5-cyclooctadiene)nickel(O) to triethylphosphine is in the range of about 4:1 to about 1:4, preferably about 1:2. Any temperature and pressure conditions can be employed which result in the production of 1,5-cyclooctadienebis(triethylphosphine)nickel(O). Generally, temperatures in the range of −50° C. to about 100° C. are employed. Preferably temperatures of about 0° C. to about 50° C. are employed. In preparing this product mixture which is subsequently contacted with hexafluorobenzene any solvent can be employed which does not adversely affect the inventive process. Examples of suitable solvents include those set forth previously as suitable for the production of the trans-fluoro(pentafluorophenyl)bis(triethylphosphine)nickel(II).

The product of this invention can be recovered by any suitable technique conventionally employed by those skilled in this art for recovering and purifying products contained in a solvent, i.e., precipitation, followed by filtration, or extraction; evaporation to dryness in vacuo, or separation of impurities by elution column chromatography followed by recrystallization.

Since the product of this invention and the reactants employed are sensitive to oxygen and/or water to varying degrees, it is preferable that suitable steps be taken to minimize the interference of those materials with the desired result. Accordingly, it is preferable that the product of this invention be prepared and used under a substantially inert atmosphere, for example, in a recirculating dry box providing a suitable inert atmosphere, i.e. an argon atmosphere.

The product of this invention being a halo(haloorgano)bis(triorganophosphine)nickel complex can be employed as an olefin dimerization catalyst in accordance with the teachings of U.S. Pat. Nos. 3,686,245 or 3,689,588.

The following examples are provided to further illustrate the present invention.

EXAMPLE I

A small glass container equipped with a magnetic stirring bar was placed in a dry box and charged with 0.38 g (2.0 mmols) of hexafluorobenzene. To this container was added in a dropwise fashion a cold solution (i.e., −40° to −60° C.) of 0.55 g (2.0 mmols) of bis(1,5-cyclooctadiene)nickel(O) and 0.48 g (4.0 mmols) of triethylphosphine in 5 ml of n-hexane. The reaction mixture was allowed to stand for seven days at 30°–35°

C. The mixture was filtered to remove a brown sludge and the red-brown filtrate was cooled to −72° C. to induce crystallization. The supernatant was syringed from the yellow-brown crystals which were subsequently dried on a clay plate to give 0.07 g (7% yield) of trans-fluoro(pentafluorophenyl)bis(triethylphosphine)-nickel(II) which melted at 60°-61.5° C. Structure verification was based on elemental analysis (see below) and an infrared spectrum which was comparable to the infrared spectrum of an authentic sample of trans-bromo(pentafluorophenyl)bis(triethylphosphine)nickel(II). IR (Nujol): 2920s, 1635 vw, 1605 vw, 1490 s, 1455 ms, 1445 vs, 1435 ms, 1410 mw, 1375 mw, 1365 vw, 1345 vw, 1275 w, 1250 w, 1240 w, 1055 ms, 1040 s, 1010 w, 955 vs, 793 m, 765 ms, 734 ms, 708 vw cm$^{-1}$.

| Elemental Analysis [based on F(C$_6$F$_5$)Ni(PEt$_3$)$_2$]: | | | |
|---|---|---|---|
|  | % C | % H | % Ni |
| Calcd | 44.94 | 6.29 | 12.20 |
| Found | 44.50 | 6.71 | 12.7 |

EXAMPLE II

A small glass vial equipped with a magnetic stirring bar was placed in a dry box and charged with a mixture of 0.40 g (2 mmols) of hexafluorobenzene and 1 ml of n-hexane. To this stirred solution at 25° C. was added in a dropwise manner a solution of 1.06 g (2.0 mmols) of tetrakis(triethylphosphine)nickel(O) in 5 ml of hexane. The reaction mixture was stirred for 5 days at room temperature and on cooling to −72° C. unreacted tetrakis(triethylphosphine)nickel(O) precipitated. The reaction mixture was then heated on a stirrer-hot plate (ca. 60°-70° C.) for a few hours and then concentrated in vacuo to a yellow-brown oily residue. The infrared spectrum of this residue was comparable to that of the trans-fluoro(pentafluorophenyl)bis(triethylphosphine)-nickel(II) produced in Example I. Recrystallization of the above oil gave a yellow brown solid which exhibited essentially the same infrared spectrum as the aforementioned oily residue.

What is claimed is:

1. Trans-fluoro(pentafluorophenyl)bis(triethylphosphine)nickel(II).

2. A process comprising reacting hexafluorobenzene and a nickel complex selected from the group consisting of tetrakis(triethylphosphine)nickel(O), ethylenebis(triethylphosphine)nickel(O), and 1,5-cyclooctadienebis(triethylphosphine)nickel(O) under reaction conditions suitable for producing trans-fluoro(pentafluorophenyl)bis(triethylphosphine)nickel(II).

3. A process according to claim 2 wherein said nickel complex is tetrakis(triethylphosphine)nickel(O).

4. A process according to claim 2 wherein said nickel complex is ethylenebis(triethylphosphine)nickel(O).

5. A process according to claim 2 wherein said nickel complex is 1,5-cyclooctadienebis(triethylphosphine)nickel(O).

6. A process according to claim 3 wherein the molar ratio of hexafluorobenzene to said nickel complex is in the range of about 2:1 to about 1:1 and the temperature is in the range of about 20° C. to about 75° C.

7. A process according to claim 6 wherein said hexafluorobenzene and said nickel complex are reacted in solution in n-hexane.

8. A process according to claim 5 wherein the molar ratio of hexafluorobenzene to said nickel complex is in the range of about 2:1 to about 1:1 and the temperature is in the range of about 20° C. to about 75° C.

9. A process according to claim 8 wherein said 1,5-cyclooctadienebis(triethylphosphine)nickel(O) that is reacted is in the solution which results when bis(1,5-cyclooctadiene)nickel(O) and triethylphosphine are contacted in a solvent to produce 1,5-cyclooctadienebis(triethylphosphine)nickel(O).

10. A process according to claim 9 wherein said solution is produced by contacting bis(1,5-cyclooctadiene)nickel(O) and triethylphosphine in a molar ratio of about 1:2 at a temperature in the range of about −50° C. to about 100° C.

11. A process according to claim 2 comprising forming a solution of bis(1,5-cyclooctadiene)nickel(O) and triethylphosphine in a molar ratio of about 1:2 at a temperature in the range of about −50° C. to about 100° C. and contacting said solution with hexafluorobenzene under conditions such that trans-fluoro(pentafluorophenyl)bis(triethylphosphine)nickel(II) is produced.

12. A process according to claim 11 wherein said solution is formed by adding bis(1,5-cyclooctadiene)nickel(O) and triethylphosphine to n-hexane.

13. A process according to claim 2 wherein hexafluorobenzene and said nickel complex are reacted in solution at a temperature in the range of about 0° to about 125° C. and a pressure in the range of about 5 to about 1000 psia under a substantially insert atmosphere.

* * * * *